United States Patent [19]

Levy

[11] Patent Number: 5,650,321
[45] Date of Patent: Jul. 22, 1997

[54] IDENTIFICATION AND ISOLATION OF NEW GENES OF A BACTERIAL MULTIPLE ANTIBIOTIC RESISTANCE REGULON

[75] Inventor: Stuart B. Levy, Boston, Mass.

[73] Assignee: Trustees of Tufts College, Medford, Mass.

[21] Appl. No.: 379,698

[22] Filed: Jan. 27, 1995

[51] Int. Cl.$^6$ ............... C12N 1/20; C12N 1/00; C07H 21/04
[52] U.S. Cl. ............ 435/252.3; 435/243; 435/252.33; 536/23.7
[58] Field of Search ................. 435/243, 252.3, 435/252.33; 536/23.7

[56] References Cited

PUBLICATIONS

Cohen et al. (1993) J. Bact. 175(5): 1484–1492 Dec. 13, 1996.
Cohen et al. (1989) Antimicrob. Agents and Chemotherapy. 33(8): 1318–1325.
Cohen et al. (1988) J. Bact. 170(12): 5416–5422.
Cohen et al. (1993) J. Infec. Dis. 168: 484–488.
Gambino et al. (1993) J. Bact. 175: 2888–2894.
George et al. (1993) J. Bact. 155(2): 531–540.
Greenberg et al. (1991) J. Bact. 173(14): 4433–4439.
Hachler et al. (1991) J. Bact. 173(17): 5532–5538.
Hooper et al. (1987) Am. J. Med. 82(Suppl. 4a): 12–20.
Seoane et al. (1995) J. Bact. 177(3): 530–535.
Kraus et al. (1991) Meth. Enz. 200: 546–556.

*Primary Examiner*—Robert A. Wax
*Assistant Examiner*—Lisa J. Hobbs
*Attorney, Agent, or Firm*—Wolf, Greenfield & Sacks, P.C.

[57] ABSTRACT

Methods of identifying loci and isolating genes of a bacterial multiple antibiotic resistance regulon are disclosed. In addition, isolated nucleic acids of three new genes, designated mlr1, mlr2 and mlr3, of the bacterial multiple antibiotic resistance regulon are disclosed and enabled. Transformed bacterial cells with altered expression of these new genes and methods for their use in evaluating potential antimicrobial or antibiotic compounds are also provided. Purified proteins encoded by these genes and antibodies to those proteins are also provided.

13 Claims, 1 Drawing Sheet

IDENTIFICATION AND ISOLATION OF NEW GENES OF A BACTERIAL MULTIPLE ANTIBIOTIC RESISTANCE REGULON

FIELD OF THE INVENTION

This invention relates generally to the field of antimicrobial therapy. In particular, this invention relates to methods of identifying and isolating loci and genes in bacteria or other microbes which affect antibiotic or antimicrobial susceptibility or resistance and to the production of bacterial strains useful in the field of antimicrobial therapy. Finally, this invention relates to isolated nucleic acids involved in antibiotic or antimicrobial susceptibility in bacteria and cells transformed therewith.

BACKGROUND OF THE INVENTION

Antibiotic or antimicrobial substances have long been used to inhibit the growth of bacteria or other microbes and to treat bacterial or microbial infections in humans, other animals, and in tissue culture. The use of antibiotics or antimicrobials in a treatment regimen, however, has the undesirable effect of selecting for bacteria or other microbes which are resistant to those antibiotics or antimicrobials which are administered or applied. As a result, treatment regimens can be adversely affected or, in some cases, rendered ineffective. This necessitates a continual search for new antibiotics and antimicrobials.

Of particular interest is the discovery of bacteria which express a multiple antibiotic resistance phenotype (Mar). This phenotype entails simultaneous resistance to a multiplicity of antibiotics which are unrelated in chemical structure. The appearance of such bacteria and infections by such bacteria greatly increase the difficulty of identifying effective antibiotics and treating infections in humans or other animals.

Multiple antibiotic resistance in bacteria is most commonly associated with the presence of plasmids which contain one or more resistance genes, each encoding a single antibiotic resistance phenotype (Clewell 1981; Foster 1983). Multiple antibiotic resistance associated with the chromosome, however, has been reported in *Klebsiella, Enterobacter, Serratia* (Gutmann et al. 1985), *Neisseria* (Johnson and Morse 1988), and *Escherichia* (George and Levy 1983a).

Bacteria expressing the multiple antibiotic resistance phenotype can be isolated by selecting bacteria with a single antibiotic and then screening for cross-resistance to structurally unrelated antibiotics. For example, George and Levy initially described a chromosomal multiple antibiotic resistance system which exists in *Escherichia coli* and which can be selected by a single drug, e.g., tetracycline or chloramphenicol (George and Levy 1983a). In addition to resistance to the selective agents, the Mar phenotype includes resistance to structurally unrelated agents, including nalidixic acid, rifampin, penicillins, and cephalosporins (George and Levy 1983). More recently, resistance to the fluoroquinolones has been described (Cohen et al. 1989).

The expression of a Mar phenotype, conferring substantially increased, simultaneous and coordinated resistance to a multiplicity of structurally unrelated compounds, appears to involve coordinated changes in the expression of a multiplicity of genes. This has been demonstrated in Mar phenotype bacteria of the species *E. coli* (Cohen et al. 1989). Such coordinated control of the expression of a multiplicity of genes implies the existence of an operon which directly or indirectly regulates the expression of the multiplicity of genes directly responsible for the Mar phenotype. One such operon was identified in *E. coli* and named marA by George and Levy (George and Levy 1983b).

Prior to the present invention, however, no multiple antibiotic resistance (mar) operon had been isolated or cloned. In addition, no mar operon had been characterized as to its structure and operation so as to enable the use of such an operon or its fragments for diagnostic, therapeutic or experimental purposes. Furthermore, the genes subject to regulation by such an operon, themselves constituting a "mar regulon" had never been identified, isolated, or cloned.

SUMMARY OF THE INVENTION

The present invention provides methods of identifying bacterial loci and isolating bacterial genes which affect resistance to antibiotic compositions and the expression of the Mar phenotype.

In one such method, an activator of a bacterial mar operon is contacted with a sample of bacterial DNA and sites on the DNA which bind the activator are identified.

In another method, an operable nucleotide sequence encoding an activator of mar operon is introduced within bacteria and loci are identified for which there is a changes in the level of expression in response to the activator.

In addition, two marker-fusion methods of identifying such loci are provided.

In the first, bacteria are subjected to a first set of conditions such that they express a Mar phenotype and a nucleotide sequence including a promoterless marker gene is introduced within the bacteria. After permitting the marker to integrate at random sites within bacterial chromosome, bacteria in which the marker is expressed are isolated. These bacteria are then subjected to a second set of conditions such that they do not express the Mar phenotype. The bacteria which cease to express the marker under the second set of conditions are then isolated and the sites of integration of the marker gene are determined. By using a temperature-sensitive plasmid to produce the Mar phenotype under the first set of conditions (by encoding an activator of a mar operon or by encoding anti-sense to a repressor of a mar operon), the plasmid and the phenotype may be lost for the second set of conditions by raising the temperature.

In the second marker-fusion method, the conditions are reversed in that the bacteria are first subjected to conditions under which they do not express the Mar phenotype and are then subjected to conditions under which they do. In this method, the bacteria which do not express the marker under the first set of conditions but which do express it under the second set are isolated and the sites of integration of the marker are determined. By exposing the bacteria to an inducer of the mar operon, the second conditions may conveniently be produced from the first.

The invention also provides isolated nucleic acids and cloned genes for three loci which affect resistance to antibiotic compositions and the expression of the Mar phenotype and which form part of a mar regulon. These genes have been designated mlr1, mlr2, and mlr3 genes.

Thus, the present invention provides isolated nucleic acid sequences comprising mlr1, mlr2, and mlr3 genes. In a particular embodiment, the invention provides isolated nucleic acid sequences comprising mlr1, mlr2, and mlr3 genes of *Escherichia coli* genome.

The present invention also provides isolated mlr1, mlr2 and mlr3 genes, and isolated *E. coli* mlr1, mlr2 and mlr3 genes in particular, which hybridize under stringent hybridization conditions to complements of particular disclosed sequences in the appended Sequence Listing.

The present invention also provides isolated mlr1, mlr2 and mlr3 genes, and isolated *E. coli* mlr1, mlr2 and mlr3 genes in particular, which hybridize under stringent hybridization conditions to portions of the *Escherichia coli* chromosome at approximate map positions of 32.7–32.8, 13.8, and 53.7–53.8 minutes, respectively.

The present invention also provides isolated mlr1, mlr2 and mlr3 genes, and isolated *E. coli* mlr1, mlr2 and mlr3 genes in particular, which hybridize under stringent hybridization conditions to Kohara phage numbers 273 and 274, 166 and 167, and 413 and 414, respectively.

The present invention also provides an isolated mlr1 gene, and an isolated *E. coli* mlr1 gene in particular, which encodes a protein which causes increased susceptibility to at least one of ampicillin, tetracycline, and nalidixic acid.

The present invention also provides an isolated mlr2 gene, and an isolated *E. coli* mlr2 gene in particular, which encodes a protein which causes decreased susceptibility to tetracycline.

The present invention also provides an isolated mlr3 gene, and an isolated *E. coli* mlr3 gene in particular, which encodes a protein which causes decreased susceptibility to ampicillin and/or tetracycline.

The present invention also provides an isolated mlr1 gene, and an isolated *E. coli* mlr1 gene in particular, which is positively regulated by expression of a bacterial mar operon.

The present invention also provides an isolated mlr2 gene, and an isolated *E. coli* mlr2 gene in particular, which is positively regulated by expression of a bacterial mar operon.

The present invention also provides an isolated mlr3 gene, and an isolated *E. coli* mlr3 gene in particular, which is positively regulated by expression of a bacterial mar operon.

The present invention also provides for transformed cells. In particular, the invention provides for bacterial cells which have been transformed with any of the isolated nucleic acids or genes described above. Thus, the invention provides for cells with increased or decreased or differently regulated mlr1, mlr2 or mlr3 genes. The invention further provides for bacterial cells which have been transformed by any of isolated nucleic acids or genes described above joined to a regulatory region so as to be operable. The regulatory regions may, in particular, be the endogenous regulatory regions of the mlr1, mlr2, and mlr3 genes. In addition, they maybe exogenous regulatory regions such as are provided by expression vectors.

The present invention further provides for bacterial cells in which an endogenous mlr1, mlr2, or mlr3 gene has been rendered inoperable or deleted.

The present invention also provides for methods of evaluating potential antibiotic compositions. In one method, a bacterial cell possessing at least one operable mlr1, mlr2 or mlr3 gene, is contacted or exposed to the composition assays for changes in the expression of the mlr gene(s) are conducted. In another method, a bacterial cell possessing at least one marker gene operably joined to a regulatory region of a mlr1, mlr2 or mlr3 gene is contacted or exposed to the composition assays for changes in the expression of the marker gene are conducted. Lastly, the invention provides methods in which a bacterial cell possessing at least one mlr1, mlr2 or mlr3 gene which has been recombinantly altered to affect its expression is contacted with the composition the survival or reproduction of the cell is determined.

The invention further provides substantially pure protein encoded mlr1, mlr2, and mlr3 genes and, in particular, protein encoded by *E. coli* mlr1, mlr2 and mlr3 genes.

Finally, the invention provides substantially pure antibodies which selectively bind to protein encoded mlr1, mlr2, and mlr3 genes and, in particular, protein encoded by *E. coli* mlr1, mlr2 and mlr3 genes.

DEFINITIONS

Figure 1:
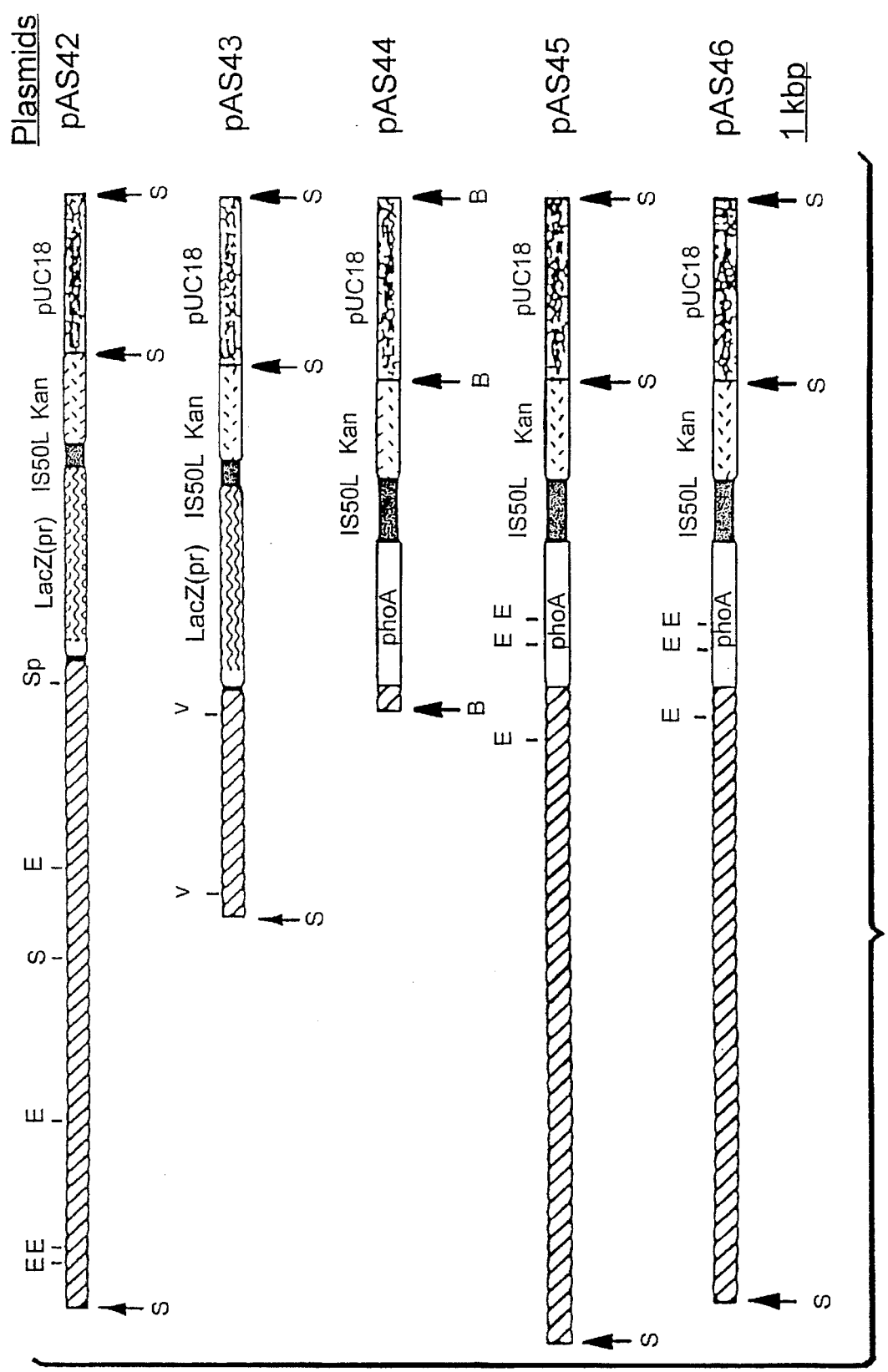
FIG. 1. Restriction enzyme map of plasmids carrying mar-regulated insertions. pAS42 and pAS43 contain a lacZ gene fusion. The hatched bar indicates chromosomal DNA; the open bar upstream of the lacZ gene corresponds to the 254 bp of phoA gene. pAS44, pAS45 and pAS46 contain phoA fusions. Abbreviations for restriction enzymes are as follows: E, EcoRI; B, BamHI; S, SalI; Sp, SphI; V, EcoRV.

In the description that follows, a number of terms used in biochemistry, molecular biology and recombinant DNA technology are extensively utilized. In addition, certain new terms are introduced for greater ease of exposition and to more clearly and distinctly point out the subject matter of the invention. In order to provide a clear and consistent understanding of the specification and claims, including the scope to be given such terms, the following definitions are provided.

By a "gene" is understood a nucleotide sequence encoding a peptide. A gene consists of a start codon, a stop codon and at least one codon encoding an amino acid residue between the start and stop codons. Typically, a gene is transcribed to produce an mRNA transcript and that transcript is translated to produce a peptide. The fixed position of a gene on a chromosome is referred to as its "locus."

By "regulatory region" is understood a nucleotide sequence involved in regulating the transcription of one or more genes. Regulatory regions will include a promoter sequence at which an RNA polymerase may bind and, typically, an operator sequence which may be bound by a repressor protein. Additionally, regulatory regions may include enhancers of transcription.

By "operon" is understood one or more genes operably joined to a regulatory region such that, under appropriate conditions, an RNA polymerase may bind to a promoter sequence in the regulatory region and proceed to transcribe the genes. The genes within an operon share a common regulatory region and, therefore, are substantially regulated as a unit. Amongst the genes in an operon may be a repressor gene which encodes a repressor protein which, under appropriate conditions, binds to the operator of the operon so as to substantially decrease expression of the genes in the operon.

By "regulon" is understood two or more genes in two or more different operons whose expression is regulated by a common repressor or activator protein. A "first" operon may, for example, encode a repressor protein which, under appropriate conditions, binds to the operators of two or more different operons so as to substantially inhibit transcription of the genes within those operons. Or, a "first" operon may encode an activator protein which interferes with the activity of one or more repressors of two or more different operons so as to substantially increase the transcription of the genes within those operons. Alternatively, a "first" operon may encode a protein which affects the translation or activity of proteins encoded by one or more genes in two or more different operons. In each of these cases, the latter operons form a regulon which is regulated by a common protein product or products of the "first" operon.

By a "bacterial multiple antibiotic resistance regulon" ("mar regulon") is understood a regulon encoding a multiplicity of protein products which are regulated in expression or activity by a common protein product and which can cause a substantial increase in resistance to a multiplicity of antibiotics, at least some of which antibiotics are unrelated structurally.

By a "bacterial multiple antibiotic resistance operon" ("mar operon") is understood a bacterial operon which, by its expression, affects the expression of two or more different operons which form a mar regulon. That is, by a "bacterial multiple antibiotic resistance operon" is understood a bacterial operon which, by its expression, affects the expression of two or more genes in two or more different operons, or which affects the activity of two or more protein products of such genes, so as to substantially increase resistance to a multiplicity of antibiotics, at least some of which are structurally unrelated. Amongst the genes in a bacterial multiple antibiotic resistance operon, there is at least one gene encoding an activator of a bacterial multiple antibiotic resistance regulon. Amongst the genes in a bacterial multiple antibiotic resistance operon, there may also be a gene encoding a repressor of the bacterial multiple antibiotic resistance operon. The mar operon of E. coli includes the marO region and marR, marA and marB genes and, therefore, is also referred to as the marRAB operon. The nucleotide sequence of one E. coli marRAB operon is disclosed in U.S. patent application Ser. No. 08/225,480 and in Cohen, S. P., H. Hachler and S. B. Levy, J. Bact. 175:1484–1492 (1993), the entire disclosures of which are incorporated herein by reference.

By a "repressor of a bacterial multiple antibiotic resistance operon" ("mar repressor" or "MarR") is understood a protein which, under appropriate conditions, binds to the operator of the operon so as to substantially inhibit the transcription of the operon. Such repressor proteins are encoded by repressor genes of bacterial multiple antibiotic resistance operons.

By an "activator of a bacterial multiple antibiotic resistance regulon" ("mar activator" or "MarA") is understood a protein encoded by a gene within a mar operon which, under appropriate conditions, affects the expression of two or more genes in a mar regulon or the activity of two or more proteins from such a regulon so as to cause expression of a bacterial multiple antibiotic resistance phenotype.

By an "enhancer of a bacterial multiple antibiotic resistance regulon" ("mar enhancer" or "MarB") is understood a protein encoded by a gene within a mar operon which, under appropriate conditions, enhances the expression or activity of a mar activator so as to increase expression of a bacterial multiple antibiotic resistance phenotype.

By a "bacterial multiple antibiotic resistance phenotype" ("Mar phenotype") is understood simultaneous and coordinated resistance to a multiplicity of antibiotics, at least some of which are structurally unrelated, which is substantially increased relative to typical or wild-type bacteria. The antibiotic resistance is simultaneous and coordinated in that the resistance to the multiplicity of antibiotics increases or arises simultaneously and may be decreased or lost simultaneously.

By a "marker gene" is understood a gene whose expression is easily assayed. A marker gene is typically a gene encoding an enzyme and the assay may include a substance which changes color in the presence of a product of the enzyme's activity. Alternatively, a marker gene may encode a protein which directly or indirectly affects a visually apparent phenotype of an organism such as color or colony type in bacteria. Alternatively, a marker gene may encode a protein which directly or indirectly confers substantial resistance to, sensitivity to, or dependence upon a particular composition.

By "expression" of a gene is understood the transcription of the gene to produce mRNA and the translation of the mRNA transcript to produce a peptide. By "substantially decreased expression of a gene" is understood a decrease in detectable expression of its mRNA transcript and/or protein product of at least about 10% and preferably more than 25% of the previous level. By "substantially increased expression of a gene" is understood an increase in the level of its mRNA transcript and/or protein product of at least about 10% and preferably about 25% of the previous level.

By an "operable" gene is understood a gene capable of being transcribed under appropriate conditions in vivo or in vitro. A gene or nucleotide sequence is "operably joined" to a regulatory region if, under appropriate conditions, an RNA polymerase may bind to the promoter of the regulatory region and proceed to transcribe the gene or nucleotide sequence in an appropriate reading frame. A gene or nucleotide sequence operably joined to a regulatory region is operable.

A coding sequence and a regulatory region are said to be operably joined when they are covalently linked in such a way as to place expression of the coding sequence under the influence or control of the regulatory sequence. Two DNA sequences are said to be operably joined if induction of the promoter function of one results in the transcription of an mRNA sequence corresponding to the coding sequences of the other. If it is desired that the RNA transcript be translated into a protein or polypeptide, there are further considerations. A coding sequencing which is to be translated into a protein or polypeptide is said to be operably joined to a regulatory region if induction of the promoter results in the transcription of an mRNA transcript corresponding to the coding sequences and if the nature of the linkage between the two DNA sequences does not (1) result in the introduction of a frame-shift mutation, (2) interfere with the ability of the regulatory sequences to initiate and promote the transcription of the coding sequences, or (3) interfere with the ability of the mRNA template to be translated into a functional protein. Thus, a regulatory region would be operably joined to a DNA sequence if the promoter were capable of effecting transcription of that DNA sequence such that the resulting transcript might be translated into a functional protein or polypeptide.

If it is not desired that the coding sequence be eventually expressed as a protein or polypeptide, as in the case of anti-sense RNA expression, there is no need to ensure that the coding sequences and regulatory region are joined without a frame-shift. Thus, a coding sequence which need not be eventually expressed as a protein or polypeptide is said to be operably joined to a regulatory region if induction of promoter function results in the transcription of an mRNA sequence corresponding to the coding sequences.

The precise nature of the regulatory region needed for gene expression may vary between species or cell types, but shall in general include, as necessary, 5' non-transcribing and 5' non-translating (non-coding) sequences involved with initiation of transcription and translation respectively, such as a TATA box, capping sequence, CAAT sequence, and the like. Especially, such 5' non-transcribing regulatory sequences will include a region which contains a promoter for transcriptional control of the operably joined coding sequences. Such regulatory regions may also include enhancer sequences or upstream activator sequences, as desired.

By "homology" of nucleotide sequences is understood a correlation in the nucleotide composition and ordering of the sequences. If the composition and ordering of the nucleotides are the same or substantially the same, the sequences are characterized by "sense" homology. If the composition and ordering of the nucleotides of the sequences are substantially complementary such that the sequences may, under appropriate conditions, hydrogen bond in the manner of complementary strands of DNA, the sequences are characterized by "anti-sense" homology. Sequences characterized by sense homology to the mRNA transcript of a gene may, under appropriate conditions, bind to the DNA of that gene so as to inhibit further transcription. Sequences characterized by anti-sense homology to the mRNA transcript of a gene may, under appropriate conditions, bind to the DNA of that gene so as to inhibit further transcription or bind to the mRNA transcript of that gene so as to inhibit translation.

Two nucleotide sequences are substantially homologous if one of them or its anti-sense complement can bind to the other under strict hybridization conditions so as to distinguish that strand from all or substantially all other sequences in a cDNA or genomic library. Alternatively, one sequence is substantially homologous to another if it or its anti-sense complement is useful as a probe in screening for the presence of its homologous DNA or RNA sequence under strict hybridization conditions. "Stringent hybridization" conditions is a term of art understood by those of ordinary skill in the art. For any given nucleotide sequence, stringent hybridization conditions are those conditions of temperature and buffer solution which will permit hybridization of that nucleotide sequence to its complementary sequence and not to substantially different sequences. The exact conditions which constitute "stringent" conditions, depend upon the length of the nucleotide sequence and the frequency of occurrence of subsets of that sequence within other non-identical sequences. By varying hybridization conditions from a level of stringency at which no hybridization occurs to a level at which hybridization is first observed, one of ordinary skill in the art can, without undue experimentation, determine conditions which will allow a given sequence to hybridize only with perfectly complementary sequences. Hybridization conditions which permit hybridization to imperfectly complementary sequences are employed to isolate nucleotide sequences which are allelic to or evolutionary homologs of any given sequence. Suitable ranges of such stringency conditions are described in Krause, M. H. and S. A. Aaronson, *Methods in Enzymology*, 200:546–556 (1991). By a sequence which is "substantially homologous" to some specified sequence is understood a sequence which will hybridize to the specified sequence, its allelic variants and evolutionary homologs under stringent hybridization conditions so as to distinguish those sequences from non-allelic, non-homologous sequences.

By an "anti-sense gene" is understood a gene which encodes an mRNA transcript characterized by substantial anti-sense homology to the mRNA encoded by a specified gene. An anti-sense gene to an activator gene of a bacterial multiple antibiotic resistance operon, for example, will encode an mRNA transcript characterized by substantial anti-sense homology to the mINA transcript encoded by the activator gene. The anti-sense mRNA may bind to the DNA of the activator gene so as to inhibit further transcription or it may bind to the mRNA transcript of the activator gene so as to inhibit translation.

By "antibiotic" is understood a chemical composition or moiety which decreases the viability or which inhibits the growth or reproduction of microbes. As used in this disclosure, for simplicity of exposition, antibiotics are intended to embrace antibacterial, antiviral, antifungal and, generally, antimicrobial compositions.

By an "isolated" nucleotide sequence or "isolated" nucleic acid is understood a nucleotide sequence which has been: (1) amplified in vitro by, for example, polymerase chain reaction (PCR); (2) recombinantly produced by cloning; (3) purified, as by cleavage and gel separation; or (4) synthesized by, for example, chemical synthesis. An isolated nucleotide sequence is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleotide sequence existing in its native state in its natural host is not. An isolated nucleotide sequence may be substantially purified, but need not be. For example, a nucleotide sequence that is isolated within a cloning or expression vector is not pure in that it may comprise only a tiny percentage of the material in the cell in which it resides. Such a nucleotide sequence is, however, isolated as the term is used herein because it is readily manipulable by standard techniques of recombinant DNA technology known to those of ordinary skill in the art.

DETAILED DESCRIPTION OF THE INVENTION

The present invention provides methods for identifying loci and cloning or isolating genes involved in the expression of a Mar phenotype other than mar operons. That is, the invention provides methods of identifying loci and cloning or isolating genes which form part of a mar regulon. The methods all depend upon use of the nucleotide sequences or protein products of a mar operon. In preferred embodiments, the mar operon is the *E. coli* mar operon or marRAB operon.

In addition to these methods, the present invention provides for isolated nucleic acids of three novel genes of the mar regulon of *E. coli*. The invention also provides for cells transformed with these nucleic acids, assays employing the nucleic acids and transformed cells, substantially purified proteins encoded by these nucleic acids, and antibodies to these proteins.

Exemplary methods of identifying mar regulon loci are disclosed: (1) a method in which a mar activator protein, or MarA, is used to select DNA which binds the activator, (2) a method in which mRNAs are selected on the basis of increases or decreases in expression in response to the expression of a mar operon, and (3) a method in which random insertions of a promoterless marker are used to identify loci whose expression is affected by expression of a mar operon.

In the first embodiment, substantially purified mar activator protein (MarA) is mixed with the fragmented genomic DNA of a species under conditions which permit it to bind to appropriate DNA sequences. DNA fragments to which the activator has bound may then be isolated on filters, in polyacrylamide gels, or by other methods well known to those of ordinary skill in the art. Those fragments may then be cloned into vectors and used as probes to locate and isolate their corresponding genes or may be sequenced to identify gene products associated with them.

In the second embodiment, a cell line is employed into which has been introduced a vector bearing an operable mar activator gene such that the cells express the Mar phenotype. Preferably, the activator gene is joined to a regulatory region other than the mar regulatory region such that its level of expression is high. Alternatively, the mar repressor gene may be inactivated by deletion, insertion or substitution and a plasmid bearing an operable activator gene but not an operable repressor gene may be introduced within the cells. The total mRNA from these cells may then be compared to the total mRNA of cells which are not expressing the Mar phenotype. In a most preferred embodiment, this is accomplished by creating a cDNA library of the total mRNA from the mar strain and the non-mar strain. This cDNA library is then used to generate probes to screen, by standard Northern technique, the total mRNA from the mar strain and the non-mar strain. Any cDNA probes that hybridize to the mRNA of one strain but not to the mRNA of the other will correspond to genes involved in the expression of the Mar phenotype. Those probes may then be used to identify such genes by standard techniques. An alternative approach would employ subtractive screening. The cDNA from a strain expressing a mar activator gene can be hybridized to excess mRNA from a strain deleted of that gene. Subsequently, those cDNAs which do not hybridize can be isolated by, for example, hydroxyapatite chromatography and used to identify mar related genes.

In the third and preferred embodiment, a promoterless and therefore inoperable marker gene is introduced into cells and allowed to insert randomly into the chromosome. The cells are then manipulated so as to change their phenotype either from non-Mar to Mar or from Mar to non-Mar. Cells in which the expression of the marker changes along with the change in Mar phenotype, contain markers which have operably inserted into genes which are regulated directly or indirectly by a mar operon. The two alternative versions of this embodiment are described separately, below.

In one version of the above embodiment, the cells do not initially express the Mar phenotype but contain an operable mar operon which is capable of being induced. It is particularly preferred that a vector bearing an operable mar repressor gene be introduced within the cells such that the expression of the mar activator gene is initially minimal. A promoterless marker gene contained within a transposon and inserted within a phage, for example λ::TnphoA or λ::TnlacZ, is introduced into the cells and allowed to randomly integrate into the genome. In addition, it is desirable that the transposon also include a gene conferring resistance to kanamycin or another appropriate antibiotic. A number of colonies, preferably at least two thousand and, more preferably, at least ten thousand, are then isolated on plates containing kanamycin or another appropriate antibiotic. These colonies are then examined for expression of the marker gene. If the marker is phoA or lacZ and the cells are grown on plates with 5-bromo-4-chloro-3-indolyl phosphate (XP plates) or 5-bromo-4-chloro-3-indolyl β-D-galactoside (XG plates), colonies in which the marker operably inserted into an actively expressed gene will be blue whereas colonies in which the marker failed to insert, inserted inoperably, or inserted operably into a repressed gene will appear white. The colonies in which the marker is not expressed are then isolated and the cells are grown in the presence of a known inducer of the mar operon (e.g. salicylate or tetracycline for E. coli). Subsequent to such treatment, colonies which express the marker (and, in this example, turn blue) are isolated. These colonies contain the marker operably inserted in a gene that is subject to regulation by a mar operon. The DNA of these colonies may then be fragmented and cloned. Those clones which confer resistance to kanamycin or another appropriate antibiotic will contain the marker in the transposon as well as DNA adjacent to the insertion site. The genomic DNA adjacent to the insertion site of the transposon can then be isolated and the gene into which the transposon inserted can be identified by techniques known to those of ordinary skill in the art. That gene will, by this method, be identified as one which is involved in the expression of the Mar phenotype.

In a most preferred version of the above embodiment, the cells initially express the Mar phenotype but can easily be caused to express the non-Mar phenotype. As above, a promoterless marker in a transposon is introduced within the cells and allowed to randomly integrate into the chromosome. And, as above, the transposon also encodes a gene conferring resistance to kanamycin or another appropriate antibiotic. A temperature sensitive plasmid, such as pMAK705 (Hamilton, et al. 1989), bearing an operable mar activator gene is introduced within the cells. The plasmid may bear the activator gene operably joined to a mar regulatory region but without the mar repressor gene or, preferably, may contain an activator gene operably joined to a regulatory region other than a mar regulatory region such that its level of expression is high. If the mar activator gene is operably joined to a mar regulatory region, the chromosomal mar repressor gene must be inactivated by any of the means disclosed above. In addition, the chromosomal mar activator gene is inactivated by any of the means disclosed above so that the expression of the Mar phenotype is dependent upon the plasmid copy of the activator gene and the cells are recombination deficient (e.g. recA$^-$) so that the activator gene on the plasmid cannot be introduced into the chromosome. Initially, the cells are grown at a temperature at which the temperature sensitive plasmid replicates (e.g. 30° C. for pMAK705) and in the presence of kanamycin or another appropriate antibiotic. In this embodiment, a number of colonies, preferably at least two thousand and, more preferably, at least ten thousand, are then isolated and examined for expression of the marker gene. If the marker is phoA or lacZ and the cells are grown on X-P or X-G plates, for example, colonies in which the marker operably inserted into an actively expressed gene will be blue whereas colonies in which the marker failed to insert, inserted inoperably, or inserted operably into a repressed gene will appear white. The colonies in which the marker is expressed are then isolated and the cells are grown at an elevated temperature (e.g. 42° C. for pMAK705) such that the temperature sensitive plasmid and, consequently, the Mar phenotype are lost. Then, colonies which no longer express the marker are isolated. These colonies contain the marker in the transposon operably inserted in a gene that is subject to regulation by a mar operon. As described above, the kanamycin or other resistance gene in the transposon can be used to isolate a fragment containing the transposon and DNA adjacent to the insertion site of the transposon. The gene into which the transposon inserted can then be identified by techniques known to those of ordinary skill in the art. That gene will, by this method, be identified as one which is involved in the expression of the Mar phenotype.

To identify genes regulated by the marRAB operon and involved in the Mar phenotype in E. coli, the marker fusion approach, essentially as described above with TnphoA (22) and TnlacZ (32), was used. Fusions in which β-galactosidase or alkaline phosphatase expression changed when the mar operon was removed were isolated. As a result of these studies, four mar locus-regulated (mlr) genes, three of which have not previously been described, were identified and the corresponding nucleic acids were isolated. These three new genes have been designated mlr1, mlr2 and mlr3. The details of the experimental protocol used are described in the experimental section below.

As used herein, the abbreviations "mlr1", "mlr2" and "mlr3" refer to the *E. coli* mlr1, mlr2 and mlr3 genes and their homologs amongst the enterobacteria.

The *E. coli* mlr1 gene maps to approximately 32.7 to 32.8 minutes of the *E. coli* chromosome. A partial sequence of 187 base pairs of the coding strand of one allele is disclosed as SEQ ID NO.:1. This sequence has been shown to hybridize to overlapping phages 273 and 274 of a Kohara collection of phages. Thus, without undue experimentation, using the information of SEQ ID NO.:1, one of ordinary skill in the art is enabled to obtain and isolate the entire sequence of mlr1 from *E. coli* genomic or cDNA or from the ordered miniset collection of clones of a Kohara collection using phages 273 and 274.

The *E. coli* mlr2 gene maps to approximately 13.8 minutes of the *E. coli* chromosome. A partial sequence of 174 base pairs of the coding strand is disclosed as SEQ ID NO.:2. This sequence has been shown to hybridize to overlapping phages 166 and 167 of a Kohara collection of phages. Thus, without undue experimentation, using the information of SEQ ID NO.:2, one of ordinary skill in the art is enabled to obtain and isolate the entire sequence of mlr2 from *E. coli* genomic or cDNA or from the ordered miniset collection of clones of a Kohara collection using phages 166 and 167.

The *E. coli* mlr3 gene maps to approximately 53.7 to 53.8 minutes of the *E. coli* chromosome. A partial sequence of 164 base pairs of the coding strand is disclosed as SEQ ID NO.:3. This sequence has been shown to hybridize to overlapping phages 413 and 414 of a Kohara collection of phages. Thus, without undue experimentation, using the information of SEQ ID NO.:3, one of ordinary skill in the art is enabled to obtain and isolate the entire sequence of mlr3 from *E. coli* genomic or cDNA or from the ordered miniset collection of clones of a Kohara collection using phages 413 and 414.

The full nucleotide sequences of the mlr1, mlr2, and mlr3 genes, and isolated nucleic acids comprising these sequences, may be obtained by a variety of methods well known in the art. The *E. coli* mlr1, mlr2, and mlr3 genes ("mlr genes") are obtainable from *E. coli* genomic DNA, from cDNA to *E. coli* mRNA, or from libraries of *E. coli* genomic or cDNA (e.g. a Kohara collection of phage containing overlapping clones of portions of the *E. coli* genome).

One may, for example, use each of the isolated nucleic acids of SEQ ID NO.:1 through SEQ ID NO.:3 as probes to isolate an *E. coli* mRNA transcribed from the corresponding mlr gene. Using reverse transcription of the selected mRNA, one may then obtain an isolated nucleic acid comprising the mlr gene.

Alternatively, one may use the isolated nucleic acids of SEQ ID NO.:1 through SEQ ID NO.:3 as PCR and sequencing primers to sequence *E. coli* genomic or library DNA in both the 5' and 3' directions until a full sequence for the corresponding mlr gene is obtained. As is well known in the art, if DNA from a library of clones is employed as the source material for the sequencing, the full sequence may span two or more clones. The sequences derived from the two or more clones then may be combined to produce a single sequence and single isolated nucleic acid containing the full mlr gene. Thus, with mlr1 as an example, the entire mlr1 sequence may be contained in Kohara phage 274. If, however, the open reading frame of the mlr1 gene appears to extend beyond the end of the clone of phage 274, one of ordinary skill may continue sequencing in Kohara phage 273 until the remainder of the mlr1 gene is obtained. The two partial sequences may then be aligned and a single sequence comprising the full mlr1 sequence produced. Because the sequenced fragments of each of the newly identified mlr genes hybridized to two Kohara phages, if the phages are used as the source DNA for obtaining the full mlr genes, it is likely that each gene will span the two phages. Conversely, given the size of the *E. coli* inserts in each Kohara phage, it is virtually certain that no more than the two phages indicated for each gene will be needed to obtain full sequences.

One of ordinary skill in the art will easily recognize a complete mlr gene sequence as one beginning with an initiation codon, extending through a significant open reading frame and ending with a termination codon. A bacterial regulatory region will be found 5' to the open reading frame but may be separated from the mlr gene by one or more additional open reading frames if the mlr gene is part of a larger transcriptional unit or operon.

The mlr1, mlr2 and mlr3 genes of *E. coli* will be capable of hybridizing under strict hybridization condition to a nucleic acid complementary to SEQ ID NO.:1, SEQ ID NO.:2 or SEQ ID NO.:3, respectively. Similarly, the mlr1, mlr2, and mlr3 genes of *E. coli* will be capable of hybridizing under stringent hybridization conditions to the corresponding Kohara phage clones listed above for each of these three genes. Finally, the mlr1, mlr2, and mlr3 genes of *E. coli* will be capable of hybridizing under stringent hybridization conditions to nucleic acids isolated from the corresponding *E. coli* chromosome map positions indicated above for each of these three genes.

As explained in the experimental section below, the TnphoA or TnlacZ insertions into the three new mlr genes resulted in an altered antibiotic susceptibility profile. Thus, these newly identified loci and isolated genes are shown to be useful targets and compositions for the alteration of the antibiotic susceptibility or resistance of bacteria.

Thus, in one series of embodiments, the isolated nucleic acids comprising the mlr1, mlr2 and mlr3 genes may be operably joined to regulatory regions so as to produce operable mlr1, mlr2 and mlr3 genes and these may be introduced into bacterial cells so as to alter their susceptibility or resistance to antibiotics and/or to create bacterial cells in which the expression of the mlr1, mlr2 and mlr3 genes is altered.

The regulatory regions which may be operably joined to the mlr1, mlr2 and mlr3 genes may be the endogenous mlr regulatory regions. On the basis of the sequences disclosed herein, as well the disclosed map positions of the mlr genes on the *Escherichia coli* chromosome, one of ordinary skill in the art is enabled to identify and isolate the endogenous regulatory regions for each of these genes. These regulatory regions will either be 5' to the mlr genes or may be separated by one or more open reading frames of additional genes in the same transcriptional unit or operon. Regulatory regions may be recognized by one of skill in the art by reference to well known consensus sequences which characterize such regions.

Alternatively, the mlr genes may be operably joined to exogenous regulatory sequences which, when introduced into a bacterial cell, will provide for altered expression of the mlr genes. Transcriptional initiation regulatory sequences can be selected which allow for repression or activation, so that expression of the operably joined sequences can be modulated. Such regulatory sequences include regulatory sequences which are temperature-sensitive so that by varying the temperature, expression can be repressed or initiated, or which are subject to chemical regulation by inhibitors or inducers. In addition, regulatory regions may be selected which cause constitutive expression.

The recombinant genes of the invention are introduced into cells using vectors. Almost any conventional bacterial delivery vector can be used. Such vectors are now widely available commercially and it is within the knowledge and discretion of one of ordinary skill in the art to choose an appropriate vector. The sequences may be introduced into such a cell on a self-replicating vector or may be introduced into the bacterial chromosome by homologous recombination or by an insertion element such as a transposon.

Depending upon which strand of the coding sequence is operably joined to the regulatory sequences it is possible to express the normal mlr mRNA for subsequent translation into the normal mlr translation product or to produce anti-sense RNA which can inhibit expression of an endogenous mlr on the bacterial chromosome. Thus, the present invention also provides for isolated mlr anti-sense genes and cells transformed with mlr anti-sense genes.

In another series of embodiments, the present invention provides for bacterial cells which are free of an endogenous operable mlr1, mlr2 or mlr3 gene on the bacterial chromosome. In a preferred embodiment, a strain is created which has a deletion, insertion or substitution in an endogenous chromosomal mlr gene such that the gene is no longer capable of being transcribed, the transcription product is no longer capable of translation, or the translation product is no longer a functional protein (e.g. as a result of a frame-shift insertion/deletion). In a particularly preferred embodiment, a deletion is introduced. This may be achieved by any means known in the art. Preferably, the deletion is introduced by cloning a mlr gene into a temperature sensitive plasmid which replicates at lower temperatures but does not replicate at higher temperatures. Using appropriate restriction enzymes, any one of numerous possible deletions is introduced into the mlr gene on the plasmid. The plasmid is then introduced into bacterial cells and the cells are grown at the lower temperature to allow for homologous recombination to introduce the partially deleted mlr gene into the bacterial chromosome. The bacteria are then grown at the higher temperature so that, at cell division, the temperature sensitive plasmid is lost from the daughter cells. Cells into which the deletion was introduced into the chromosome may then be selected. In a similar fashion, or by other means known in the art, substitutions and additions may be introduced to a mlr gene which will produce a bacterial cell free of an operable mlr gene on the bacterial chromosome.

As examples of this particular embodiment, the isolated nucleic acids of SEQ ID NO.:1, SEQ ID NO.:2 and SEQ ID NO.:3 may be used to introduce changes which will inactivate or render inoperable E. coli mlr1, mlr2 and mlr3 genes, respectively. Thus, for example, restriction enzymes may be used to introduce a deletion into SEQ ID NO.:1 or, alternatively, a synthetic oligonucleotide may be produced which corresponds to SEQ ID NO.:1 with a deletion or insertion. This sequence may then be used to homologously recombine with the endogenous chromosomal mlr1 gene of E. coli so as to render the chromosomal gene inoperable and to create a bacterial strain free of an endogenous operable mlr1 gene on the chromosome.

Thus, bacterial cells overproducing the gene products of any one or more of the mlr1, mlr2 and mlr3 genes, or any combination of these genes, can be made by introducing additional operable copies of the gene(s) into such cells by well known methods. Likewise, bacterial cells unable to produce the gene products of any one or more of the mlr genes, or any combination of these genes, can be made by "knocking out" the endogenous chromosomal gene or by interfering with its expression by introducing a corresponding anti-sense gene. Finally, the expression of one or more of the mlr genes, or any combination of these genes, may be selectively altered by introducing recombinant constructs with exogenous regulatory regions which are inducible or repressible by easily manipulable experimental variables (e.g. a lacZ promoter system). For example, the endogenous chromosomal mlr gene can be rendered inoperable (preferably by a large deletion) and a replacement mlr gene may be introduced on a plasmid operably joined to an inducible or repressible exogenous promoter. Alternatively, an anti-sense construct may be introduced in which the anti-sense gene is operably joined to an inducible or repressible exogenous promoter.

In another series of embodiments, the present invention also provides methods for testing or screening compositions for potential use and effectiveness as antibiotics.

In particular, as the mlr genes of the present invention are part of a mar regulon and changes in their expression are involved in the development of the Mar phenotype, one set of embodiments involves the use of an assay in which cells are contacted with or exposed to the test composition and changes in the level of expression of the mlr genes is assayed as an indication of the potential effectiveness of the compositions. These changes in the level of expression of the mlr genes may be determined by standard methods such as methods directed to levels of mlr encoded mRNA transcripts or levels of mlr encoded proteins. In addition, a marker-fusion approach may be employed in which a marker gene is operably joined to the regulatory regions of a mlr gene and expression of the marker is assayed rather than expression of the mlr gene.

Alternatively, the recombinantly altered cells of the present invention, with increased, decreased or otherwise altered expression of an mlr gene, may be used to test the efficacy of potential antibiotic compositions by exposing the cells to the composition and by assessing the effects on the survival or reproduction of those cells. Such assays are well known in the art and include, for example, an assay of MIC (minimal inhibitory concentration) as shown in the experimental section below. By using the recombinantly transformed cells of the present invention, one can assess the potential effectiveness of antibiotic compositions depending upon the level of expression of the recombinantly altered mlr gene. Thus, compositions may be identified which are particularly effective or particularly ineffective in combating cells with different levels of mlr gene expression.

The present invention also provides probes useful in identifying mlr loci and isolating mlr genes in species other than E. coli. A cloned mlr gene or cloned fragment of a mlr gene from one species can be used to screen a DNA, cDNA or other library of another species to identify mlr genes by methods which are known to those of ordinary skill in the art. DNA homologous to the E. coli marRAB operon has been found among many members of the Enterobacteriaceae including Klebsiella (Cohen, Yah and Levy, 1993). Similarly, induction of the Mar phenotype by salicylate and acetyl salicylate has been commonly observed among 58 clinical enteric isolates tested (Foulds and Rosner, personal communication). In Klebsiella, Serratia and *Pseudomonas cepacia*, the salicylate decreased the presence of OmpF-like outer membrane porins (Burns and Clark, 1992; Sawai, Hirano and Yamaguchi, 1987). Furthermore, in Klebsiella, salicylates increased resistance to various antibiotics (including B-lactams and tetracycline), decreased resistance to aminoglycosides and decreased the amounts of capsular polysaccharide (Domenico, Hopkins and Cunha, 1990) Domenico, Landolphi and Cunha, 1991). This indicates that mar operons are involved in salicylate induction of Mar phenotypes in many enterobacteria. Given the ubiquity and conservation of mar operons, one of ordinary skill in the art will have a high expectation of success in identifying and isolating the genes of these species which are subject to regulation by the mar operon, namely, the mlr genes.

The present invention in another aspect provides substantially pure protein encoded by a mlr1 gene, substantially pure protein encoded by a mlr2 gene, and substantially pure protein encoded by a mlr3 gene. In particular, the invention provides substantially pure E. coli mlr1 protein, substantially pure E. coli mlr2 protein and substantially pure E. coli mlr3 protein. Substantially pure proteins are suitable for protein sequencing and are typically at least 90% pure by weight and preferably at least 95% pure by weight. Given the sequences disclosed and enabled herein, as well as the methods provided for identifying homologous mlr genes in other species, such substantially pure proteins can be produced and isolated by one of ordinary skill in the art (Maniatis, et al. 1982). These proteins may be used, for example, as immunogens to produce antibodies.

Finally, the present invention provides for antibodies, including monoclonal antibodies and active fragments of antibodies, to mlr proteins. Using the substantially pure mlr proteins of the present invention, one of ordinary skill in the art is enabled to produce antibodies to these proteins. See, for example, Catty, D. *Antibodies, A Practical Approach*, Vol. 1, IRL Press, Washington, DC (1988); Klein, J. *Immunology: The Science of Cell-Noncell Discrimination*, John Wiley & Sons, New York (1982); Kennett, R., et al. in *Monoclonal Antibodies, Hybridoma: A New Dimension in Biological Analyses*, Plenum Press, New York (1980); Campbell, A., "Monoclonal Antibody Technology," in *Laboratory Techniques in Biochemistry and Molecular Biology*, Volume 13 (Burdon, R., et al., eds.), Elsevier, Amsterdam (1984); and Eisen, H. N., in *Microbiology*, 3rd Ed. (Davis, B. D., et al., eds.) Harper & Row, Philadelphia (1980). The antibodies of the present invention may be used, for example, in the above-described assays to measure levels of mlr gene product expression and for further purification of the mlr proteins.

EXPERIMENTAL METHODS

Material and Methods

Bacterial strains, plasmids and phages

Bacterial strains and plasmids used in this study are listed in Table 1. The 1.24 kbp BspH1 deletion in the mar locus in strain ASS110 was made by homologous recombination following methods described (17), using pWY4, a derivative of the temperature sensitive plasmid pMAK705, bearing the deletion. The presence of the deletion in the recipient strain was verified by Southern blot analysis using the deleted fragment as a specific probe. The strain was made recAl by P1 transduction of the mutation in association with srl::Tn10 from LM303 as previously described (23) and selected on plates containing tetracycline. The presence of the recAl mutation in the recipient strain was verified by its sensitivity to killing by irradiation with 300 ergs/cm$^2$ of 254 nm U.V. light. Cells in which Tn10 had spontaneously excised (making them tetracycline susceptible) were identified after enrichment for Tc$^s$ derivatives among cells growing logarithmically in 7.5 µg/ml of tetracycline after the addition of 20 µg/ml of ampicillin to kill the Tc$^r$ growing cells. The recAl tetracycline-sensitive strain was called ASS111.

Plvir came from the laboratory collection. The λTnSphoA and λTn5lacZ (pr) were obtained from B. Wanner (Purdue University, West Lafayette, Ind.).

These phages are defective in both replication and lysogenization (λ c1857 b221Pam3 rex:TnphoA)(32). The λTn5lacZ (pt) used was λTn5A'-4 (31) which contains 254 bp in common with λTn5phoA in the left end and has the kanamycin resistance (Kan$^r$) gene from Tn5. Strain AW1045 came from A. Wright (Tufts University School of Medicine, Boston, Mass.). The insertions will be referred to as TnphoA and TnlacZ herein.

Plasmid pAS10 was constructed by cloning a 2.5 kbp PCR-generated fragment from the mutant (marR5) mar locus on pHHM193 into the temperature-sensitive plasmid pMAK705. The resulting plasmid constitutively expressed the marRAB operon as well as transcriptional unit 1 consisting of orf64 and orf157 (see ref. 6).

Media and chemicals

Cells were grown in LB broth (10 g of tryptone per liter, 5 g of yeast extract per liter, 5 g of NaCl per liter). Selective media were prepared by using antimicrobial agents at the following concentrations: chloramphenicol, 25 µg/ml; kanamycin, 50 µg/ml; tetracycline, 12 µg/ml. The blue dyes 5-bromo-4-chloro-3-indolyl phosphate (X-P) and 5-bromo-4-chloro-3-indole-β-D-galactopyranoside (X-Gal), for detecting alkaline phosphatase and β-galactosidase activities, were obtained from Sigma Chemical Co.(St. Louis, Mo.) and used at a concentration of 40 µg/ml.

Antibiotic susceptibility assays

Antibiotic susceptibility was measured by a gradient plate method (9) on LB agar using cultures grown to logarithmic growth phase in LB broth. The minimal inhibitory concentration (MIC) was estimated by the limit of confluent growth after incubation of plates for 36–48h at 30° C.

Genetic techniques

Chromosomal and plasmid DNA isolation, DNA transformation, DNA transfer and hybridization, analysis with restriction endonucleases, T4 DNA ligase, and DNA labeling were performed as described (4,16,26).

DNA sequencing was performed (27) with Sequenase kit (U.S. Biochemicals Corp). The oligonucleotide 5'CCA-GAACAGGGCAAAAC3' was used to sequence the upstream chromosomal DNA junctions of phoA and lacZ insertions cloned into plasmids.

For hybridization to the gene mapping membranes (Takara Biochemical Inc., Berkeley, Calif.), 100 µl of chloroform:isoamyl alcohol [24:1] and 100 µl of diethylpyrocarbonate (to inactivate possible nucleases) were added to each 100 µl of solution containing the $^{32}$P-labeled DNA probes. After hybridization, membranes were washed twice in 2xSSC (1xSSC is 0.15M NaCl and 0.0015M sodium citrate) for 5 min at room temperature, followed by two 30-min washes in 2xSSC+1% SDS (sodium dodecyl sulfate) at 65° C. and two 15-min washes in 0.1xSSC at room temperature. The films were exposed to x-ray film overnight. Membranes were not allowed to dry during exposure in order to permit removal of the radiolabeled probes by boiling in 0.5% SDS for 5–10 min.

Isolation of TnphoA and TnlacZ insertions

To isolate mutants with chromosomal TnphoA or TnlacZ insertions, we infected 5×10$^8$ ASS111 cells bearing plasmid pAS10, grown to logarithmic phase at 30° C. in the presence of chloramphenicol, with 5 µl of phage lysate:λTn5phoA at a titer of $2\times10^{10}$ plaque forming units (PFU) per ml (multiplicity of infection around 0.2) or $5\times10^{10}$ PFU of λTn5lacZ (pr). Cells infected by the phages were plated at 30° C. on Kan to identify chromosomal insertionsN The transfection frequency was $0N5\times10^{-4}$ for λTnSphoA and $0.8\times10^{-4}$ for λTn5lacZ (pr). Of the $Kan^4$ colonies from the mutagenesis, 2% with λTnSphoA were blue on X-P agar and 11% from the mutagenesis with λTn5lacZ (pr) were blue on X-Gal agar.

β-Galactosidase and alkaline phosphatase assays

Whole cells were grown to logarithmic phase at 30° C. in LB medium. β-galactosidase activity was assayed using ONPG as substrate after permeabilization with SDS/chloroform and incubation for 60 min, as previously described (23). The alkaline phosphatase activity of cultures was measured in SDS/chloroform-treated cells using p-nitrophenol phosphate (PNPP) as substrate (15). In both assays, one unit represents 0.222 μmol of substrate converted per min per A600 unit of cells.

For phoA fusions, the activity in membrane and supernatant fractions was also determined. Pellets from cells grown to logarithmic phase were resuspended in 50 mM Tris-HCl (pH 8)+10 mM EDTA (pH 8)+100μg/ml lysozyme and disrupted by gentle sonication on ice. After ultracentrifugation at 40K for 1 h, membrane pellets were resuspended by sonication in 0.2M Tris (pH 8)-2%Triton X-100. Alkaline phosphatase activity of supernatant and membrane fractions was assayed without SDS/chloroform.

Cloning of phoA and lacZ fusions

Total chromosomal DNA of ASS112, ASS113, ASS115 and ASS116 strains was digested with SalI and ligated with similarly digested pUC18 and transformed into strain DH5α with selection for simultaneous ampicillin and kanamycin resistance, forming the plasmids pAS42, pAS43, pAS45 and pAS46, respectively (FIG. 1). The chromosomal DNA from ASS114 was digested with BamHI and ligated with BanHI-digested pUC18, using the same selection described above; plasmid pAS44 was obtained (FIG. 1). Chromosomal DNA and the DNA of the corresponding plasmids digested with the same enzymes were separated by electrophoresis in agarose and blotted to a nylon membrane, and probed with a $^{32}$P-labeled 0.92 kbp PstI fragment of Tn5 from plasmid pAS1 (29). The same pattern of hybridization was seen in each of the original insertion mutants and its derivative plasmid (data not shown), confirming that the correct fragments had been cloned.

Results

Identification of TripboA and TnlacZ insertions into genes controlled by the mar locus 2100 fusions (820 phoA fusions and 1280 lacZ fusion) in ASS111 were randomly selected at 30° C. and screened by replica-plating at 42° C. for a change of color accompanying loss of the temperature sensitive plasmid pAS10 containing the mar locus. Five were identified and studied further. Two of these fusions, ASS112 and ASS113, containing a lacZ fusion, showed a loss of color upon loss of the mar locus on plasmid pAS10 at 42° C. The other three mutants, ASS114, ASS115 and ASS116, containing a phoA fusion, showed an increase of color upon loss of the mar-containing plasmid. The mar dependence of each strain was verified by a return to the original color phenotype upon reintroduction of pAS10 into the cured strain (see also Tables 2,3 below). The negative control was introduction of the vector alone.

Mapping of fusions regulated by the mar operon on the chromosome of *E. coli*

We used endonuclease digestion with SalI or BamHI which cleaves within Tn5, leaving an intact $Kan^r$ gene (3) to clone the junctional chromosomal fragments into pUC18. A nylon membrane containing the ordered miniset collection of clones of a Kohara collection of phages was hybridized with the radiolabeled chromosomal DNA Tn5 junctional fragments cloned from the five fusions (FIG. 1). The 3.2 kbp EcoRI-SpHI chromosomal fragment from the plasmid pAS42 derived from the lacZ fusion contained in ASS112 strain hybridized with the overlapping phages 273 and 274, which contained sequences from approximately min 32.7–32.8 of the *Escherichia coli* chromosomal map (20). The 3.6 kbp EcoRV chromosomal fragment in pAS43, cloned from the lacZ fusion in strain ASS113, was mapped to the overlapping phages 166 and 167 containing sequences from approximately min 13.8 of the *E. coli* map.

The phoA fusion contained in ASS114 strain was mapped at approximately min 53.7–53.8 by using the 5.2 kbp BamHI fragment from the plasmid pAS44, which hybridized with phages 413 and 414. The fragment used for the hybridization also contained the phoA gene and, therefore, also hybridized with phages 142 and 143 corresponding to 1A10 and 6A12 from the Kohara collection.

Finally, the phoA fusions present in ASS115 and ASS116 were mapped by using the 9 kbp EcoRI-SalI fragment from the plasmids pAS45 and pAS46 (FIG. 1). This band is the same in both plasmids and hybridized in both cases with the overlapping phages 607, 608 and 609, indicating that both fusions are at min 77 of the *E. coli* map. The genes identified were given the designation mlr1→5 (mar locus regulated).

Sequencing and gene identification of cloned junctional chromosomal fragments

About 200 bp of TnphoA or TnlacZ junctional chromosomal fragments from each plasmid were sequenced. The sequences of all five were different. The DNA and all possible putative protein sequences obtained were compared with other DNA and protein sequences in the GenBank using the FASTA method in the GCG package of sequence analysis programs (24). Homology was noted between the fragments on pAS45 and pAS46 and the newly-described slp gene for a lipoprotein in *E. coli* (1). No homology was found for the other cloned fragments with genes in the databank. Three partial gene sequences (identified in ASS112 (mlr1::TnlacZ), ASS113 (mlr2::TnlacZ), ASS114 (mlr3::TnphoA) were given accession numbers in GenBank: mlr1=ECU09712; mlr2=ECU09713, mlr3=ECU09714. These same sequences are disclosed herein as SEQ ID NO.:1, SEQ ID NO.:2 and SEQ ID NO.:3.

Expression of the mar-regulated gene fusions

The strains containing the lacZ and phoA fusions were examined for β-galactosidase and alkaline phosphatase expression in the presence or absence of the pAS10 plasmid. The β-galactosidase activity in ASS112 strain was increased 94-fold by the pAS10 plasmid (Table 2), but no change was observed with the plasmid vector alone (pMAK705). Enzyme activity in ASS113 was increased 40-fold by the plasmid containing the mar operon. These results suggest that the mar locus is needed for expression of the genes fused with lacZ in these strains.

In contrast, a repressive effect of the mar locus was observed with the phoA fusions present in ASS114, ASS115 and ASS116 strains (Table 3). A large effect was observed in ASS115 and ASS116, with 126-fold and 98-fold less alkaline phosphatase activity in the presence of plasmid pAS10 than the strain alone or in the presence of vector plasmid pMK705. A much smaller effect (a 4.3-fold decrease) was noted with the ASS114 (pAS10) strain.

A change in expression of LacZ and PhoA was also observed on X-P and X-Gal plates when only MarA, the activator protein encoded by the marA gene of the mar operon (11,31,33) was introduced on a high-copy plasmid into the 5 different strains. No change was observed when the repressor of the mar operon, MarR, was introduced on a high copy plasmid (data not shown). The latter findings indicate that the genes can be regulated by MarA alone, although they do not rule out an additive role for other genes in the mar locus.

The physical location of the mar-responsive phoA fusion proteins was determined by cell fractionation. In ASS115, approximately 80% of the alkaline phosphatase activity was membrane-associated. In ASS114 and ASS116, most of the activity was released into the supernatant. Since PhoA must be periplasmic to be active, the fusions are presumably in a membrane or periplasmic protein. In the case of ASS115 and AS116, the gene product, Slp, is known to be periplasmic and probably also in the outer membrane (1).

Antibiotic susceptibility phenotype

Since the transposon insertions were responsive to the mar operon, we examined the effect of each insertion on antibiotic susceptibility. All fusions showed an altered antibiotic susceptibility profile, whether in the absence or presence of the mar operon on pAS10 (Table 4). In the absence of the plasmid, effects independent of the mar locus could be seen. Although most differences were small (10–40%), some were 2 fold. As compared to the parental ASS111, ASS112 consistently showed 2 fold decreased susceptibility to tetracycline and nalidixic acid and about 1.3 fold to ampicillin, with little if any change in susceptibility to chloramphenicol and norfloxacin. ASS113 showed increased susceptibility to tetracycline, but little change in susceptibility to the other antibiotics. The three PhoA fusions, ASS114→ASS116 showed increased susceptibility to ampicillin, tetracycline, nalidixic acid and norfloxacin (Table 4).

When plasmid pAS10, bearing the complementing mar locus, was added to ASS111, resistance levels to all antibiotics increased. The plasmid, however, was unable to restore the wild-type drug susceptibility profile in the insertion strains. Compared to ASS111 (pAS10) mutant ASS112 (pAS10) showed increased susceptibility to ampicillin, tetracycline and norfloxacin, but retained a decreased susceptibility to nalidixic acid. ASS113 with pAS10 showed less than wild-type MIC to tetracycline, but approximately wild-type (~10% less) to the other drugs. The plasmid in ASS114 produced wild-type or higher MIC values to all antibiotics (Table 4). In ASS115 and ASS116, the plasmid produced similar results with generally the same or slightly less than wild-type MIC to all drugs tested.

mlr1: The Tn5 insertion in this gene (strain ASS112) makes $E.\ coli$ more resistant to several antibiotics: two times more resistant to ampicillin and nalidixic acid, and three times more resistant to rifampin.

mlr2: The Tn5 insertion in this gene (strain ASS113) makes the $E.\ coli$ strain a third more sensitive to tetracycline as compared to wild type when induced by the mar locus.

mlr3: The Tn5 insertion in this gene (strain ASSS114) makes the $E.\ coli$ strain slightly more sensitive to oxidative stress agents (paraquat and phenazine methosulfate) in the absence of Mar induction. Complementation studies, in which mlr3 has been cloned on a 3.5 kb HindIII-KpnI fragment into pSPORT1 and then introduced into ASS114, gives two fold higher levels of resistance to paraquat and phenazine methosulfate as compared to ASS114 alone. Cloning this fragment into pSPORT1 is the presently preferred mode of isolating mlr3 from $E.\ coli$.

TABLE 1

Bacterial Strains and Plasmids

| Strain or Plasmid | Relevant Characteristic(s) |
|---|---|
| E. Coli | |
| AW1045 | Derivative of MC4100,F− araD139 ΔlacU169 rpsL relA thi WphoA E15 Δ(ara-leu)7679+ee |
| DH5α | supE44 ΔlacU169 (φ80 lacZ ΔM15) hsdR17 recA1 endA1 gyrA96 thi-1 relA1 |
| LM303 | met pro srl::Tn10 recA1 |
| ASS110 | AW1045 with 1.24-kbp +e,uns BspHI mar locus-specific deletion Δ(orf64/157 marORAB) |
| ASS111 | ASS110 recA1+ee |
| ASS112 | AS111 bearing a +e,uns mar-regulated lacZ gene fusion in mlr1+ee |
| ASS113 | AS111 bearing a mar-regulated +e,uns lacZ gene fusion in mlr2+ee |
| ASS114 | AS111 bearing a mar-regulated +e,uns phoA fusion in mlr3+ee |
| ASS115 | AS111 bearing a +e,uns mar-regulated phoA fusion in slp |
| ASS116 | AS111 bearing a mar-regulated phoA fusion in slp |
| Plasmids | |
| pUC18 | Multicopy vector, Ap$^r$ (reference 34) |
| pMAK705 | Temperature-sensitive cloning vector, Cml$^r$ (reference 17) |
| pWY4 | pMAK705 bearing a 9-kb PstI fragment from the chromosomal mar region in which a 1.24-kbp BspHI mar locus deletion was made (reference 33) |
| pHSG415 | Temperature-sensitive low-copy-number vector, Ap$^r$Cm$^r$Km$^r$ (reference 16) |
| pHHM193 | pHSG415 carrying the mar region on a 9-kbp chromosomal fragment with a point mutation in start codon of MarR (GTG) (marR5) (reference 5) |
| pAS1 | pUC18::(prc::Tn5) (reference 29) |
| pAS10 | pMAK705 bearing orf64 orf157 marO marRAB on a 2.5-kbp PCR product from pHHM193 |
| pAS42 | pUC18 carrying a 10-kb SalI fragment and a 60kbp SalI fragment from ASS112, Km$^r$ |
| pAS43 | pUC18 carrying an 8-kbp SalI fragment from ASS113, Km$^r$ |
| pAS44 | pUC18 carrying a 5.2-kbp BamHI fragment from ASS114, Km$^r$ |
| pAS45 | pUC18 carrying a 9-kbp SalI fragment from ASS115, Km$^r$ |
| pAS46 | pUC18 carrying a 9-kbp SalI fragment from ASS116 Km$^r$ |

TABLE 2

β-Galactosidase Activity of TnlacZ Gene Fusions in the Presence or Absence of Constitutively Expressed mar Operon

| Strain | Insertion site | Plasmid$^a$ | β-Galactosidase activity (U)$^b$ |
|---|---|---|---|
| ASS112 | mlr1 | None | 0.2 ± 0.03 |
| | | pAS10 | 18.8 ± 3.5 |
| | | pMAK705 | 0.3 ± 0.05 |
| ASS113 | mlr2 | None | 2.6 ± 0.4 |
| | | pAS10 | 102.5 ± 18 |
| | | pMAK705 | 1.4 ± 0.2 |

$^a$pMAK705, vector alone; pAS10, vector with mar locus.
$^b$Values are the means ± standard deviations based on three independent determinations.

TABLE 3

Alkaline Phosphatase Activity of
TnphoA Fusions in the Presence or Absence
of Constitutively Expressed mar Operon

| Strain | Insertion site | Plasmid[a] | Alkaline Phosphatase activity (U)[b] |
|---|---|---|---|
| ASS114 | mlr3 | None | 30.2 ± 4.5 |
|  |  | pAS10 | 7.2 ± 0.5 |
|  |  | pMAK705 | 26.5 ± 2.5 |
| ASS115 | slp | None | 37.2 ± 6.3 |
|  |  | pAS10 | 0.3 ± 0.04 |
|  |  | pMAK705 | 39.5 ± 8.5 |
| ASS116 | slp | None | 29.3 ± 4 |
|  |  | pAS10 | 0.3 ± 0.04 |
|  |  | pMAK705 | 26.6 ± 3.5 |

[a] pMAK705, vector alone; pAS10, vector with mar locus.
[b] Values are the means ± standard deviations based on three independent determinations.

TABLE 4

Changes in MICs for Tn5 Insertion Mutants

| Strain | Fold Difference in MIC of[a]: | | | | |
|---|---|---|---|---|---|
|  | AMP | TET | NAL | NOR | CML |
| ASS112 |  |  |  |  |  |
| Alone | +1.3 | +2.1 | +1.9 |  |  |
| +pAS10 |  | −0.7 | −1.4 | −0.5 |  |
| ASS113 |  |  |  |  |  |
| Alone |  | −0.8 |  |  |  |
| +pAS10 |  | −0.7 |  |  |  |
| ASS114 |  |  |  |  |  |
| Alone | −0.8 | −0.8 |  |  |  |
| +pAS10 | +1.4 | +1.2 | +1.3 |  |  |
| ASS115 |  |  |  |  |  |
| Alone | −0.7 | −0.8 | −0.7 | −0.8 |  |
| +pAS10 |  | −0.8 | −0.8 |  |  |
| ASS116 |  |  |  |  |  |
| Alone | −0.8 | −0.8 | −0.7 | −0.8 | +1.2 |
| +pAS10 |  | −0.8 | −0.7 | −0.7 |  |

[a] Fold difference in the MICs for the strains indicated as compared to ASS111 in the presence and absence of pAS10; only differences of ≧20% are noted. Results are the means for determinations for three gradient plates. The calculated MICs (in micrograms per milliliter) of the following antibiotics for ASS111 and ASS111(pAS10), respectively, were 1.8 and 8.1, ampicillin (AMP); 0.6 and 4.1 tetracycline (TET); 0.005 and 0.08, norfloxacin (NOR); 0.4 and 4.1, nalidixic acid (NAL); and 1.0 and not done chloramphenicol (CML) (chloramonrnicol could not be tested in pAS10-containing strains because Cml[r] on pAS10) +, increase in MIC; −, decrease in MIC.

REFERENCES

1. Alexander, D. M. and A. C. St. John. 1994. Characterization of the carbon starvation-inducible and stationary phase-inducible gene slp encoding an outer membrane lipoprotein in *Escherichia coli*. Molec. Microbiol. 11:1059–1071.
2. Ariza, R. R., S. P. Cohen, N. Bachhawat, S. B. Levy and B. Demple. 1994. Mutations soxQ1 and cfxB1 that activate oxidative stress genes and multiple antibiotic resistance are positioned in the marRAB operon of *Escherichia coli*. J. Bacteriol. 176:143–148.
3. Auerswald, E-A., G. Ludwig and H. Schaller. 1981. Structural analysis of Tn5. Cold Spring Harbor Symposia. Quant. Biol. 45: 107–113.
4. Beji, A., D. Izard, F. Gavini, H. Leclerc, M. Leseini-Delstanche and J. Krembel. 1987. A rapid chemical procedure for isolation and purification of chromosomal DNA from gram-negative bacilli. Anal. Biochem. 162: 18–23.
5. Cohen, S. P., L. M. McMurry and S. B. Levy. 1988. marA locus causes decreased expression of OmpF porin in multiple-antibiotic-resistant (Mar) mutants of *Escherichia coli*. J. Bacteriol. 170 :5416–5422.
6. Cohen, S. P., H. Hachler and S. B. Levy. 1993. Genetic and functional analysis of the multiple antibiotic resistance (mar) locus in *Escherichia coli*. J. Bacteriol. 175: 1484–1492.
7. Cohen, S. P., S. B. Levy, J. Foulds and J. L. Rosner. 1993. Salicylate induction of antibiotic resistance in *Escherichia coli*: activation of the mar operon and a mar-independent pathway. J. Bacteriol. 175:7856–7862.
8. Cohen, S. P., L. M. McMurry, D. C. Hooper, J. S. Wolfson and S. B. Levy. (1989). Cross-resistance to fluoroquinolones in multiple antibiotic resistant (Mar) *Escherichia coli* selected by tetracycline or chloramphenicol: decreased drug accumulation associated with membrane changes in addition to OmpF reduction. Antimicrob. Agents Chemother. 33:1318–1325.
9. Curiale, M. S. and S. B. Levy. 1982. Two complementation groups mediate tetracycline resistance determined by Tn10. J. Bacteriol. 151: 209–215.
10. Dunn, T., S. Hahn, S. Ogden and R. Schleif. 1984. An operator at −280 base pairs that is required for repression of araBAD operon promoter: addition of DNA helical turns between the operator and promoter cyclically hinders repression. Proc. Natl. Acad. Sci. USA 8: 5017–5020.
11. Gambino, L., S. J. Gracheck and P. F. Miller. 1993. Overexpression of the MarA positive regulator is sufficient to confer multiple antibiotic resistance in *Escherichia coli*. J. Bacteriol. 175:2888–2894.
12. George, A. M. and S. B. Levy. 1983. Amplifiable resistance to tetracycline, chloramphenicol, and other antibiotics in *Escherichia coli*: involvement of a non-plasmid-determined efflux of tetracycline. J. Bacteriol. 155: 531–540.
13. George, A. M. and S. B. Levy. 1983. Gene in the major cotransduction gap of *Escherichia coli* linkage map required for the expression of chromosomal resistance to tetracycline and other antibiotics. J. Bacteriol. 155: 541–548.
14. Greenberg, J. T., J. H. Chou, P. Monach and B. Demple. 1991. Activation of oxidative stress genes by mutations at the soxQ/cfxB/marA locus of *Escherichia coli*. J. Bacteriol. 173: 4433–4439.
15. Gutierrez, C., J. Barondess, C. Manoil and J. Beckwith. 1986. The use of transposon TnphoA to detect genes for cell envelope proteins subject to a common regulatory stimulus. Analysis of osmotically regulated genes in *Escherichia coli*. J. Mol. Biol. 195: 289–297.
16. Hachler, H., S. P. Cohen and S. B. Levy. 1991. marA, a regulated locus which controls expression of chromosomal multiple antibiotic resistance in *Escherichia coli*. J. Bacteriol. 173: 5532–5538.
17. Hamilton, C. M., M. Aldea, B. K. Washburn, P. Babitzke and S. R. Kushner. 1989. New method for generating deletions and gene replacements in *Escherichia coli*. J. Bacteriol. 171: 4617–4622.
18. Hanahan, D. 1983. Studies on transformation of *Escherichia coli* with plasmids. J. Mol. Biol0 166: 557–580.
19. Hoopes, B. C. and W. R. McClure.1987. Strategies in regulation of transcription initiation, p01231–1240. In F.

C. Neidhardt, J. L. Ingraham, K. B. Low, B. Magasanik, M. Schaechter, and H. E. Umbarger (ed.), *Escherichia coli and Salmonella typhimurium:* cellular and molecular biology, vol.2. American Society for Microbiology, Washington, D.C.

20. Kohara, Y., K. Akiyama and K. Isono. 1987. The physical map of the whole *Escherichia coli* chromosome: application of a new strategy for rapid analysis and sorting of a large genomic library. Cell 50: 495–508.

21. Lin, R., R. D'Ari and E. B. Newman. 1992. λ plac Mu insertions in genes of the leucine regulon: extension of the regulon to genes not regulated by leucine. J. Bacteriol. 174: 1948–1955.

22. Manoil, C. and J. Beckwith. 1985. TnphoA: A transposon probe for protein export signals. Proc. Natl. Acad. Sci. USA 82: 8129–8133.

23. Miller, J. H. 1972. Experiments in molecular genetics. Cold Spring Harbor Laboratory, Cold Spring Harbor, N.Y.

24. Pearson, W. and D. J. Lipman.1988. Improved tools for biological sequence comparison. Proc. Natl. Acad. Sci. USA. 85: 2444–2448.

25. Ptashne, M. 1992. A genetic switch, Phage λ and higher-organisms. Blackwell Scientific Publications, Cambridge, Mass.

26. Sambrook, J., E. F. Fritsch and T. Maniatis. 1989. Molecular cloning: a laboratory manual. Cold Spring Harbor Laboratory, Cold Spring Harbor, N.Y.

27. Sanger, F., S. Nicklen and A. R. Coulson. 1977. DNA sequencing with chain-termination inhibitors. Proc. Natl. Acad. Sci. USA. 74: 5463–5467.

28. Seoane, A. and S. B. Levy. 1993. Reversal of MarR binding to the regulatory region of the marRAB operon by structurally unrelated inducers. H-26, p.204, Abst. 1994 Ann. Meet. Am. Soc. Microbiol.

29. Seoane, A., A. Sabbaj, L. M. McMurry and S. B. Levy. 1992. Multiple antibiotic susceptibility associated with inactivation of the prc gene. J. Bacteriol. 174: 7844–7847.

30. Tsung, K., R. E. Brissette and M. Inouye. 1990. Enhancement of RNA polymerase binding to promoters by a transcriptional activator, OmpR, in *Escherichia coli:* its positive and negative effects on transcription. Proc. Natl. Acad. Sci. USA 87: 5940–5944.

31. White, D. G., W. Yan and S. B. Levy. 1994. Functional characterization of the chromosomal multiple antibiotic resistance (mar) locus in *Escherichia coli*. A104 p.20, Abst. 1994 Gen. Mtg. Amer. Soc. Microbiol.

32. Wilmes-Riesenberg, M. R. and B. L. Wannet. 1992. TripboA and TnphoA' elements for making and switching fusions for study of transcription, translation, and cell surface localization. J. Bacteriol. 174: 4558–4575.

33. Yan, W., S. P. Cohen and S. B. Levy. 1992. Three putative proteins in the mar operon mediate intrinsic multidrug resistance in *Escherichia coli*. Abstr. A25 p.5 Abst. 1992 Gert. Mtg. Am. Soc. Microbiol.

34. Yanisch-Perron, C., J. Vieira and J. Messing. 1985. Improved M13 phage cloning vectors and host strains: nucleotide sequences of the M13mp18 and pUC19 vectors. Gene 33: 103–119.

I claim:

1. An isolated nucleic acid comprising an Enterobacteriaceae gene selected from the group consisting of more locus regulated 1(mlr1), mlr2, and mlr3 genes.

2. The isolated nucleic acid of claim 1 wherein said gene is an *Escherichia coli* gene.

3. The isolated nucleic acid of claim 1 or claim 2 wherein said nucleic acid comprises a nucleic acid selected from the group consisting of SEQ ID NO:1, SEQ ID NO:2, and SEQ ID NO:3.

4. The isolated nucleic acid of claim 1 or claim 2 wherein said nucleic acid is a mlr1 gene which encodes a protein which causes increased susceptibility to an antibiotic selected from the group consisting of ampicillin, tetracycline, and nalidixic acid.

5. The isolated nucleic acid of claim 1 or claim 2 wherein said nucleic acid is a mlr2 gene which encodes a protein which causes decreased susceptibility to tetracycline.

6. The isolated nucleic acid of claim 1 or claim 2 wherein said nucleic acid is a mlr3 gene which encodes a protein which causes decreased susceptibility to an antibiotic selected from the group consisting of ampicillin and tetracycline.

7. The isolated nucleic acid of claim 1 or claim 2 wherein said nucleic acid is a mlr1 gene which is positively regulated by expression of a bacterial multiple antibiotic resistance operon.

8. The isolated nucleic acid of claim 1 or claim 2 wherein said nucleic acid is a mlr2 gene which is positively regulated by expression of a bacterial multiple antibiotic resistance operon.

9. The isolated nucleic acid of claim 1 or claim 2 wherein said nucleic acid is a mlr3 gene which is negatively regulated by expression of a bacterial multiple antibiotic resistance operon.

10. An Enterobacteriaceae bacterial cell into which has been introduced recombinantly an isolated nucleic acid of one of claims 1, 2, 4, 5, 6, 7, 8, or 9.

11. An Enterobacteriaceae cell into which has been introduced recombinantly an isolated nucleic acid of claims 1 or 2 wherein said nucleic acid is operably joined to a regulatory region.

12. The bacterial cell of claim 13 wherein said regulatory region is selected from the group consisting of mlr1, mlr2, and mlr3 endogenous regulatory regions.

13. An Enterobacteriaceae bacterial cell which is free of an endogenous operable gene on an Enterobacteriaceae bacterial chromosome wherein said gene is selected from the group consisting of mlr1, mlr2, and mlr3 genes.

* * * * *

UNITED STATES PATENT AND TRADEMARK OFFICE
CERTIFICATE OF CORRECTION

PATENT NO. : 5,650,321

DATED : July 22, 1997

INVENTOR(S) : Stuary B. Levy

It is certified that error appears in the above-indentified patent and that said Letters Patent is hereby corrected as shown below:

Column 2, line 24, delete "changes", insert --change-- therefor.

Column 3, line 45, delete "maybe", insert --may be-- therefor.
Column 7, line 60, delete "mINA", insert --mRNA-- therefor.
Column 14, line 60, delete "Yah", insert --Yan-- therefor.
Column 15, line 2, delete "B", insert --β-- therefor.
Column 16, line 5, delete "S", insert --5-- therefor.
Column 16, line 10, delete "(pt)", insert --(pr)-- therefor.
Column 17, line 5, delete "S", insert --5-- therefor.
Column 17, line 6, delete "Kan$^4$", and insert -- Kan$^r$--therefor
Column 17, line 7, delete "S", insert --5-- therefor.
Column 17, line 48, delete "TripboA", insert --TnphoA-- therefor.
Column 19, line 58, delete "ASSS114", insert --ASS114-- therefor.
Column 20, line 11, delete "+ee".
Column 20, line 14, delete "+e,uns".
Column 20, line 16, delete "+ee".
Column 20, line 17, delete "+e,uns".
Column 20, line 18, delete "+ee".
Column 20, line 19, delete "+e,uns".
Column 20, line 20, delete "+ee".

UNITED STATES PATENT AND TRADEMARK OFFICE
CERTIFICATE OF CORRECTION

PATENT NO. : 5,650,321
DATED : July 22, 1997
INVENTOR(S) : Stuary B. Levy

It is certified that error appears in the above-indentified patent and that said Letters Patent is hereby corrected as shown below:

Column 20, line 21, delete "+e,uns".
Column 20, line 22, delete "+ee".
Column 20, line 23, delete "+e,uns".

Column 21, line 50, delete "chloramonrnicol", insert --chloramphenicol-- therefor.
Column 22, line 65, delete "Bio10", insert --Biol.-- therefor.
Column 22, line 67, delete "pO1231-1240", insert --p.1231-1240-- therefor.
Column 24, line 26, delete "Gert.", insert --Gen.-- therefor.
Column 25, line 42, delete "more", insert --mar locus-- therefor.

Signed and Sealed this

Twenty-first Day of July, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 187 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO:1:

```
CCCCATACTC  CGCGGCTATT  CACCGGGAAT  AAATACAATT  ACCATGAATT  TAACTGTGGA      60

ATTATTTGGT  CAGGGTCGAT  AATTTATTCG  ATAAAGAATA  TCGTTGGTTC  TGTCATATGT     120

CAATCAGTCA  AACGGGCGAT  ATTACGAAAC  CTTACGCCCG  GACGAATTA   TGGTGTCGGC     180

ATGAATA                                                                   187
```

( 2 ) INFORMATION FOR SEQ ID NO:2:

( i ) SEQUENCE CHARACTERISTICS:
        ( A ) LENGTH: 173 base pairs
        ( B ) TYPE: nucleic acid
        ( C ) STRANDEDNESS: double -continued ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
 ( A ) ORGANISM: Escherichia coli ( x i ) SEQUENCE DESCRIPTION: SEQ ID NO:2:

| | | | | | | |
|---|---|---|---|---|---|---|
| CCTCAGCTCA | TTTCTTGCTC | TAATAATAGT | ATGCTGATCC | GGCGTACGGC | AAGATTCCTC | 60 |
| TGTCGAGATT | GAGTGCCAGA | TATCCTCATG | TCAGCAGAGA | ATGCTGAAGA | ACTGTTGGTT | 120 |
| CACCGAAAGC | CGATCTGGTG | ATCACCCAAA | TGCCAGTGAT | CAGCCGTTCG | TCA | 173 |

( 2 ) INFORMATION FOR SEQ ID NO:3:

( i ) SEQUENCE CHARACTERISTICS:
 ( A ) LENGTH: 164 base pairs
 ( B ) TYPE: nucleic acid
 ( C ) STRANDEDNESS: double
 ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
 ( A ) ORGANISM: Escherichia coli ( x i ) SEQUENCE DESCRIPTION: SEQ ID NO:3:

| | | | | | | |
|---|---|---|---|---|---|---|
| CTACGGTAAA | ATACAGGGAC | TTTTTAAGG | TCGCTTTGCC | CGGTGTCAAC | TCACTGTATC | 60 |
| AGGTGTAATG | AAGTCATTCA | GGCGTAACAG | TAATTACGCG | GAGAGATGTA | AAGTGAAATA | 120 |
| TTTCTTTATG | GGCATTTCTT | TTATGGTCAT | CGTTTGGGCC | GGTA | | 164 |